(12) United States Patent
Hanawa et al.

(10) Patent No.: US 9,935,023 B2
(45) Date of Patent: *Apr. 3, 2018

(54) METHODS FOR MANUFACTURING SEMICONDUCTOR DEVICE AND FOR DETECTING END POINT OF DRY ETCHING

(71) Applicant: Renesas Electronics Corporation, Tokyo (JP)

(72) Inventors: Toshikazu Hanawa, Ibaraki (JP); Kazuhide Fukaya, Ibaraki (JP); Kentaro Yamada, Ibaraki (JP)

(73) Assignee: Renesas Electronics Corporation, Koutou-ku, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/630,385

(22) Filed: Jun. 22, 2017

(65) Prior Publication Data

US 2017/0287794 A1 Oct. 5, 2017

Related U.S. Application Data

(63) Continuation of application No. 15/205,069, filed on Jul. 8, 2016, now Pat. No. 9,711,423.

(30) Foreign Application Priority Data

Aug. 27, 2015 (JP) .................................. 2015-167575

(51) Int. Cl.

| | |
|---|---|
| *G01L 21/30* | (2006.01) |
| *G01R 31/00* | (2006.01) |
| *H01L 21/66* | (2006.01) |
| *H01L 21/311* | (2006.01) |
| *H01L 21/768* | (2006.01) |
| *H01L 23/522* | (2006.01) |
| *H01L 23/532* | (2006.01) |
| *G01N 21/73* | (2006.01) |
| *G01N 21/84* | (2006.01) |

(Continued)

(52) U.S. Cl.
CPC .............. *H01L 22/26* (2013.01); *G01N 21/68* (2013.01); *G01N 21/73* (2013.01); *G01N 21/84* (2013.01); *H01J 37/32963* (2013.01); *H01L 21/31116* (2013.01); *H01L 21/76802* (2013.01); *H01L 21/76846* (2013.01); *H01L 21/76877* (2013.01); *H01L 23/5226* (2013.01); *H01L 23/5329* (2013.01); *H01L 23/53223* (2013.01); *G01N 2021/8411* (2013.01); *G01N 2021/8427* (2013.01); *G01N 2201/1247* (2013.01); *H01J 2237/334* (2013.01)

(58) Field of Classification Search
USPC ........................................................ 216/60
See application file for complete search history.

(56) References Cited

U.S. PATENT DOCUMENTS

| | | | |
|---|---|---|---|
| 4,675,072 A | 6/1987 | Bennett et al. | |
| 5,552,016 A | 9/1996 | Ghanayem | |

FOREIGN PATENT DOCUMENTS

| | | |
|---|---|---|
| JP | 8-255831 A | 10/1996 |
| JP | 2009-231718 A | 10/2009 |

*Primary Examiner* — Roberts Culbert
(74) *Attorney, Agent, or Firm* — Sughrue Mion, PLLC

(57) ABSTRACT

A via hole is accurately formed in an interlayer insulating film over a metal wiring. Of emission spectra of plasma to be used for dry etching of the interlayer insulating film, the emission intensities of at least CO, CN, and AlF are monitored such that an end point of the dry etching of the interlayer insulating film is detected based on the emission intensities thereof.

15 Claims, 7 Drawing Sheets

(51) Int. Cl.
*G01N 21/68* (2006.01)
*H01J 37/32* (2006.01)

METHODS FOR MANUFACTURING SEMICONDUCTOR DEVICE AND FOR DETECTING END POINT OF DRY ETCHING

CROSS-REFERENCE TO RELATED APPLICATIONS

This application is a continuation of U.S. application Ser. No. 15/205,069 filed Jul. 8, 2016, and claims priority from Japanese patent application No. 2015-167575 filed on Aug. 27, 2015, the disclosures of which are incorporated by reference herein in their entirety.

BACKGROUND

The present invention relates to a manufacturing method of a semiconductor device, and in particular, to a technique effective when applied to a dry etching step in which light emitted from a processing chamber is detected, and the end point of etching is detected based on a change in its emission intensity.

In semiconductor manufacturing processes, a technique is widely used, in which the end point of a process is detected by monitoring changes in plasma emission in a process chamber. Also, in dry etching steps, a light emission monitoring method is adopted as an etching end point detection method in most equipment, in which the end point of etching is detected by monitoring changes in the emission intensity of an etching gas component that emits light in plasma or in the emission intensity of a reaction product generated in plasma.

On the other hand, the area of a portion to be etched is being reduced with the miniaturization of semiconductor products, and in particular, in via hole etching for forming a via hole (contact hole) in an interlayer insulating film, such as a silicon oxide film, it becomes difficult to accurately detect an end point because of a reduction in the opening area of a via hole.

For example, in via hole etching, when it is determined that the end point of etching has been reached in the middle of the etching of an interlayer insulating, the via hole does not reach an underlying metal wiring layer, whereby a conduction defect is caused in the via. On the contrary, when a via hole reaches a metal wiring main body (aluminum film) by penetrating a barrier metal for an underlying metal wiring layer, a high-resistance layer, such as aluminum fluoride, is formed by reacting with a fluorine component contained in etching gas, which leads to a high-resistance defect in the via. To deal with these problems, various methods for increasing the accuracy of end point detection, such as monitoring in combination of emission of two wavelengths, are being considered.

For example, the technique as disclosed in Patent Document 1 is cited as a background technique of the present technical field. Patent Document 1 discloses a "technique for improving the reliability of a semiconductor device, in which a disconnection defect in the bottom of a via is prevented by prohibiting wiring having a large volume from being arranged below the via."

Additionally, Patent Document 2 discloses a "technique for stably detecting the end point of etching, in which the end point of etching is detected at a second inflection point by performing a secondary differential operation on the time series data of an emission intensity ratio between two light beams each having a wavelength."

RELATED ART DOCUMENT

Patent Document

[Patent Document 1] Japanese Unexamined Patent Application Publication No. Hei8 (1996)-255831
[Patent Document 2] Japanese Unexamined Patent Application Publication No. 2009-231718

SUMMARY

As a method for confirming the conduction state of a via, there is a method for acquiring and observing a cross-sectional SEM (Scanning-Electron-Microscope) image of the periphery of the via. When a via hole reaches a metal wiring main body (aluminum film) by penetrating a barrier metal for an underlying metal wiring layer, streaky images are obtained because the bottom of a via has a discontinuous and worm-eaten shape, an etching reaction product is attached to the bottom of a via, or the like, whereby the reaching can be confirmed from these images.

The reaching can also be confirmed by performing electrical measurement on a TEG (Test-Element-Group) arranged over a scribe after a wafer processing step is completed. An electrical property is determined by obtaining an I-V curve to calculate a resistance component and then based on a threshold value determined from a theoretical value.

However, the observation using a SEM image is micro-observation in which a very limited part over a wafer is confirmed as a representative value, and hence in such a case where pattern dependence is generated, there is the high risk that detection omission may occur. Additionally, it takes time to acquire a SEM image, and hence an inspection frequency is as low as approximately one image for every roughly 25 to 150 wafers, and hence there is the fear that a large amount of defective products may have been manufactured when abnormality is confirmed.

On the other hand, the electrical measurement on a TEG is highly sensitive; however, there is the high risk that a large amount of defective products may have been manufactured when abnormality is confirmed, similarly to the inspection using a cross-sectional SEM image, because the electrical measurement is performed after a wafer processing step is completed.

The aforementioned Patent Document 1 describes the conduction (disconnection) of the bottom of a via as a problem; however, the detection of the endpoint of etching, as described above, is not described.

The technique disclosed in the aforementioned Patent Document 2 is effective when the opening area of a via hole is reduced with miniaturization; however, a problem caused by a via hole penetrating a barrier metal, as described above, is not described.

Other problems and new characteristics will become clear from the description and accompanying drawings of the present specification.

According to one embodiment, of the emission spectra of plasma to be used for dry etching of an interlayer insulating film, the emission intensities of at least CO, CN, and AlF are monitored such that an end point of the dry etching of an interlayer insulating film is detected based on the emission intensities thereof.

According to the one embodiment, a via hole can be accurately formed in an interlayer insulating film over metal wiring. Thereby, the manufacturing yield and reliability of a semiconductor device can be improved.

BRIEF DESCRIPTION OF THE DRAWINGS

FIG. 61B is views each illustrating part of a manufacturing step of a semiconductor device according to one embodiment of the invention;

DETAILED DESCRIPTION

Hereinafter, preferred embodiments will be described with reference to views. In each view, members having the same configuration as each other are denoted with the same reference numeral, and detailed description of overlapping portions will be omitted.

First Embodiment

Figure 1:
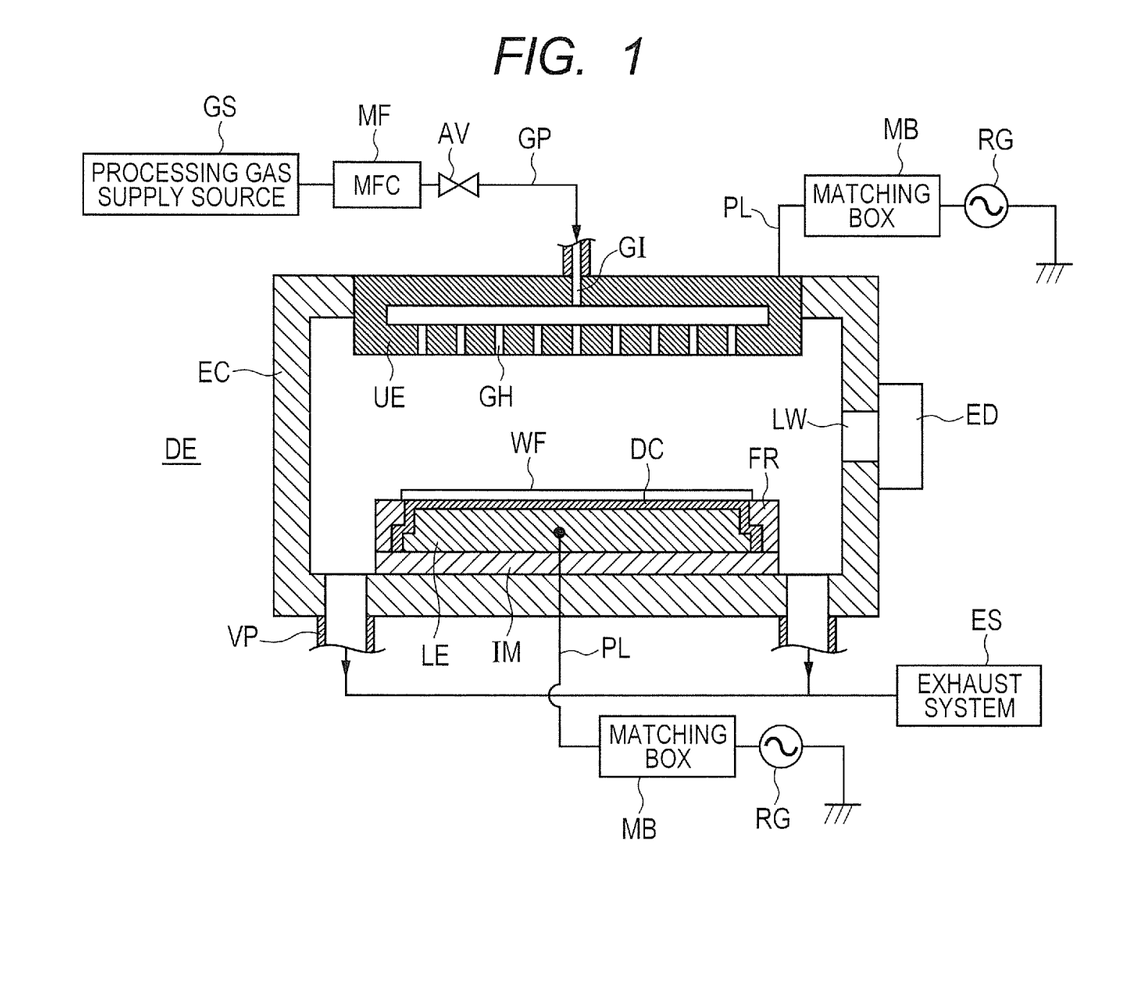
FIG. 1 is a view illustrating the outline of a dry etching apparatus according to one embodiment of the present invention.
Figure 2:
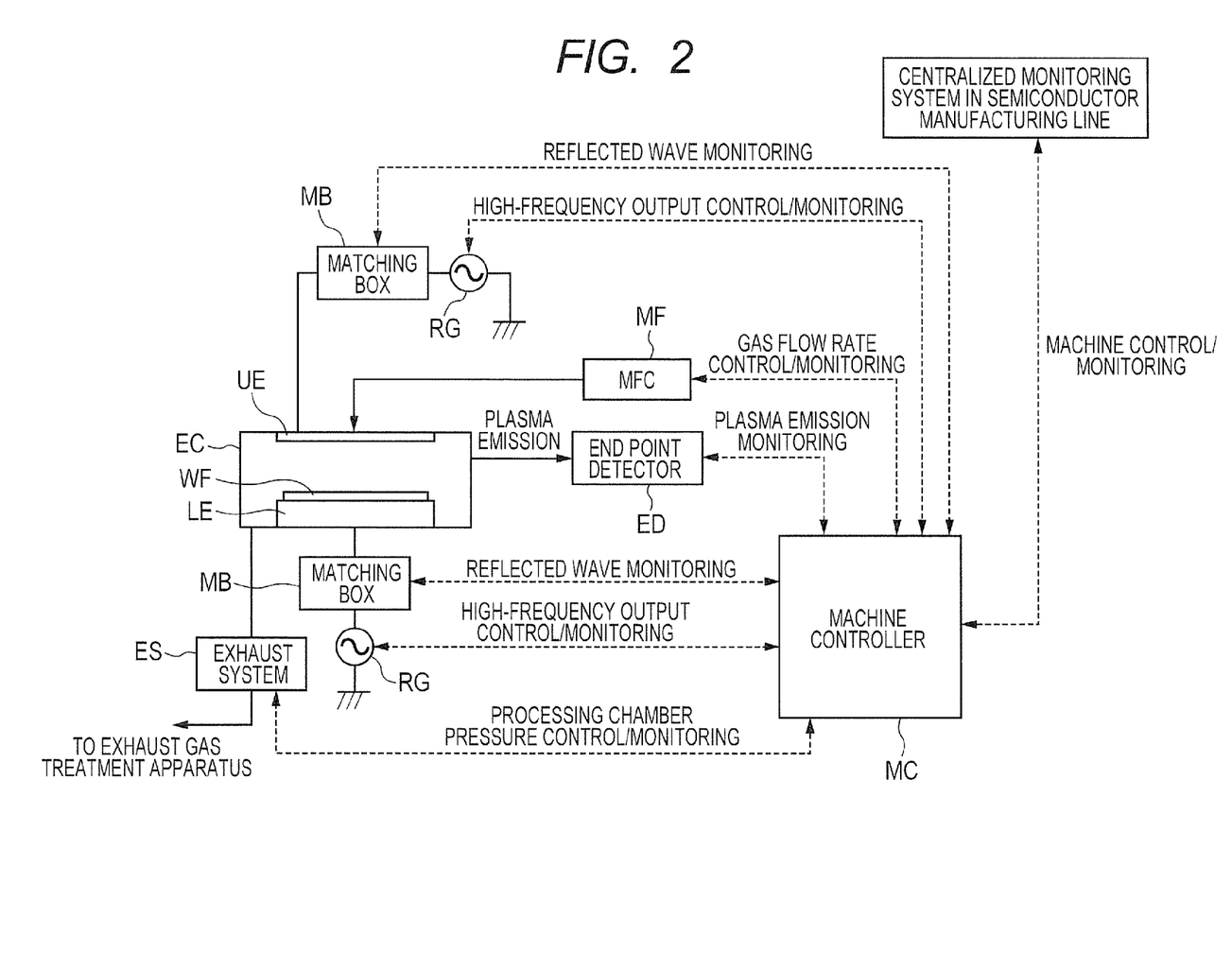
FIG. 2 is a view illustrating the outline of a control system in a dry etching apparatus according to one embodiment of the invention.
Figure 3:
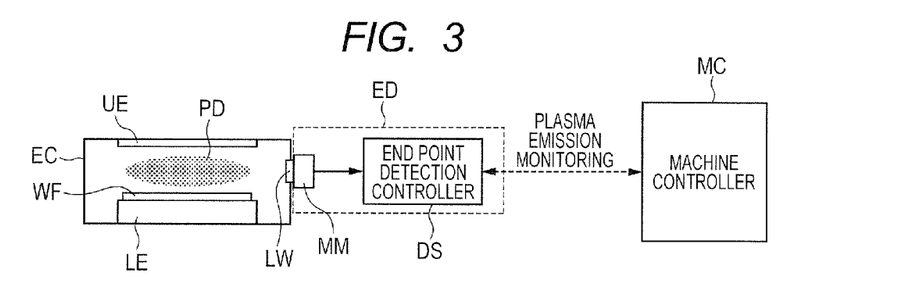
FIG. 3 is a view illustrating the outline of etching end point detection in a dry etching apparatus according to one embodiment of the invention.

A dry etching apparatus and an end point detector, according to the present embodiment, will be first described with reference to FIGS. 1 to 3. FIG. 1 is a view illustrating the whole outline of the dry etching apparatus, in which a parallel plate plasma etching apparatus is used as an example. FIG. 2 illustrates the outline of a control system in the dry etching apparatus illustrated in FIG. 1. FIG. 3 is a view schematically illustrating a configuration of an end point detector.

With reference to FIG. 1, a dry etching apparatus DE according to the present embodiment is provided, in which an upper electrode UE and a lower electrode LE face each other in a processing chamber EC. The dry etching apparatus DE has a structure in which a plurality of processing gas supply holes GH are provided in the upper electrode UE such that processing gas (etching gas) introduced from a gas introducing hole GI is supplied into the processing chamber EC. A so-called showerhead type upper electrode is provided.

The processing gas (etching gas) is supplied from a processing gas supply source GS to the gas introducing hole GI through a processing gas supply pipe GP via a mass flow controller (MFC) MF and an opening/closing valve AV.

A high-frequency power source RG is electrically coupled to the upper electrode UE by an electric supply line PL via a matching box MB such that high-frequency power from the high-frequency power source RG is supplied to the upper electrode UE via the matching box MB. The high-frequency power source RG for the upper electrodes UE outputs, for example, high-frequency power of 60 MHz.

An exhaust pipe VP is coupled to the lower portion of the processing chamber EC. The exhaust pipe VP is coupled to an exhaust system ES. The exhaust system ES is formed from a vacuum pump, such as a dry pump, a turbo molecular pump (TMP), or the like. The inside of the processing chamber EC is vacuum exhausted by adjusting an exhaust amount with the exhaust system ES. Thereby, the pressure in the processing chamber EC can be reduced to a predetermined pressure.

The lower electrode LE is installed over the bottom of the processing chamber EC via an insulating member IM. The lower electrode LE is formed, for example, by coating an alumite coat over the surface of an aluminum (AL) base material. A focus ring FR including an insulating material, such as quartz, alumina ceramic ($Al_2O_3$), or the like, is arranged around the lower electrode LE. The focus ring FR functions as a focus ring for focusing plasma on a wafer WF over the lower electrode LE and also functions as a protective ring for protecting the lower electrode LE from plasma.

A material containing a dielectric body is formed, as a dielectric coting DC, over the surface of the lower electrode LE by alumina thermal spray, and a structure is formed, in which the wafer WF is adsorbed and fixed over the lower electrode LE by electrostatic force with a direct voltage (DC voltage) being applied to the lower electrode LE (not illustrated). This structure is a so-called electrostatic chuck.

Similarly to the upper electrode UE, a high-frequency power source RG is electrically coupled to the lower electrode LE through an electric supply line PL via a matching box MB, so that high-frequency power from the high-frequency power source RG is supplied to the lower electrode LE via the matching box MB. The high-frequency power source RG for the lower electrodes LE outputs, for example, high-frequency power of 2 MHz.

A lighting window LW, by which the emission light of plasma is transmitted to the outside of the processing chamber EC while the pressure in the processing chamber EC is being maintained, is provided in the sidewall of the processing chamber EC. An end point detector ED is coupled to the lighting window LW.

The dry etching apparatus DE illustrated in FIG. 1 is formed as described above, in which, after the wafer WF is brought into the processing chamber EC and adsorbed and fixed over the lower electrode LE, the inside of the processing chamber EC is vacuum exhausted to a predetermined pressure by the exhaust system ES. Thereafter, processing gas (etching gas) is introduced into the processing chamber EC from the processing gas supply hole GH, and dry etching processing is performed on the wafer WF adsorbed and fixed over the lower electrode LE by generating plasma in the processing chamber EC with high-frequency power being applied to each of the upper electrode UE and the lower electrode LE.

FIG. 2 is a block view schematically illustrating a control system for controlling the dry etching apparatus DE illustrated in FIG. 1. In order to control and monitor each part of the dry etching apparatus DE, a machine controller MC is coupled to each of the exhaust system ES, the mass flow controller MF, the high-frequency power source RG for the upper electrodes UE, the matching box MB for the upper electrodes UE, the high-frequency power source RG for the lower electrodes LE, and the matching box MB for the lower electrodes LE, as illustrated in FIG. 2. The machine controller MC is coupled to the end point detector ED for detecting the end point of etching based on the plasma emission intensity in the processing chamber EC, so that the plasma emission intensity is monitored in order to monitor the state of plasma in the processing chamber EC.

The machine controller MC has a storage part for storing processing conditions (process recipes) in order to control each part of the apparatus ED in accordance with the processing conditions (process recipes) stored (set) in the storage part. Additionally, tolerances to the processing conditions (process recipes) are stored (set) in advance in the storage part, and when a monitored value of each part of the dry etching apparatus ED becomes more than the tolerance, it is determined that abnormality has been caused in the apparatus DE, so that an alarm is issued from the apparatus ED to the outside directly or via a centralized monitoring system in a semiconductor manufacturing line in which the apparatus DE is installed.

FIG. 3 is a view schematically illustrating the configuration of the end point detector ED in the dry etching apparatus DE illustrated in FIG. 1. As illustrated in FIG. 3, the end point detector ED is formed from both a monochromator (detector) MM for detecting the emission light of the plasma PD via the lighting window LW and an end point detection controller DS for performing operational processing on a signal detected by the monochromator (detector) MM. The monochromator is a spectroscope that extracts a wavelength within a certain wavelength range by wavelength dispersing the entered light spatially with a spectral optical element, such as a prism, a diffraction grating, or the like. Examples of the monochromator include a single monochromator that detects one specific wavelength, a double monochromator that detects two specific wavelengths, a triple monochromator that detects three specific wavelengths, a multichannel monochromator that can detect a plurality of wavelengths within a specific wavelength band range in accordance with its resolution, and the like.

Because it is necessary in the present embodiment to detect three wavelengths of at least CO ($\lambda$=226 nm), CN ($\lambda$=387 nm), and AlF ($\lambda$=396 nm), as described later, it is more preferable to use a multichannel monochromator that can continuously monitor a wavelength band of 200 nm to 800 nm.

Alternatively, one triple monochromator may be attached to the lighting window LW and coupled to one end point detection controller DS. Other methods can be considered, in which three single monochromators are used, or one single monochromator and one double monochromator are used in combination.

Alternatively, a detector, such as a photodiode, or the like, may be provided in the lighting window LW via a filter that transmits only a specific wavelength. For example, three light beams each having a wavelength can also be monitored by installing three filters, which respectively transmit only three wavelengths of CO ($\lambda$=226 nm), CN ($\lambda$=387 nm), and AlF ($\lambda$=396 nm), in parallel in the lighting window LW and by providing a photodiode over each filter.

The end point detection controller DS is provided with an operational processing function, so that it can perform a ratio operation and a secondary differential operation on the emission intensity of each detected wavelength. Herein, the ratio operation means operational processing in which a ratio of the emission intensity of a wavelength to be monitored to that of another wavelength is calculated. On the other hand, the secondary differential operation means operational processing in which a secondary differential value is calculated by further differentiating a primary differential value, which is an effective method for calculating a rate of change (degree of change). A point where a rate of change is large (inflection point) can be effectively controlled by a secondary differential operation.

Figure 4:
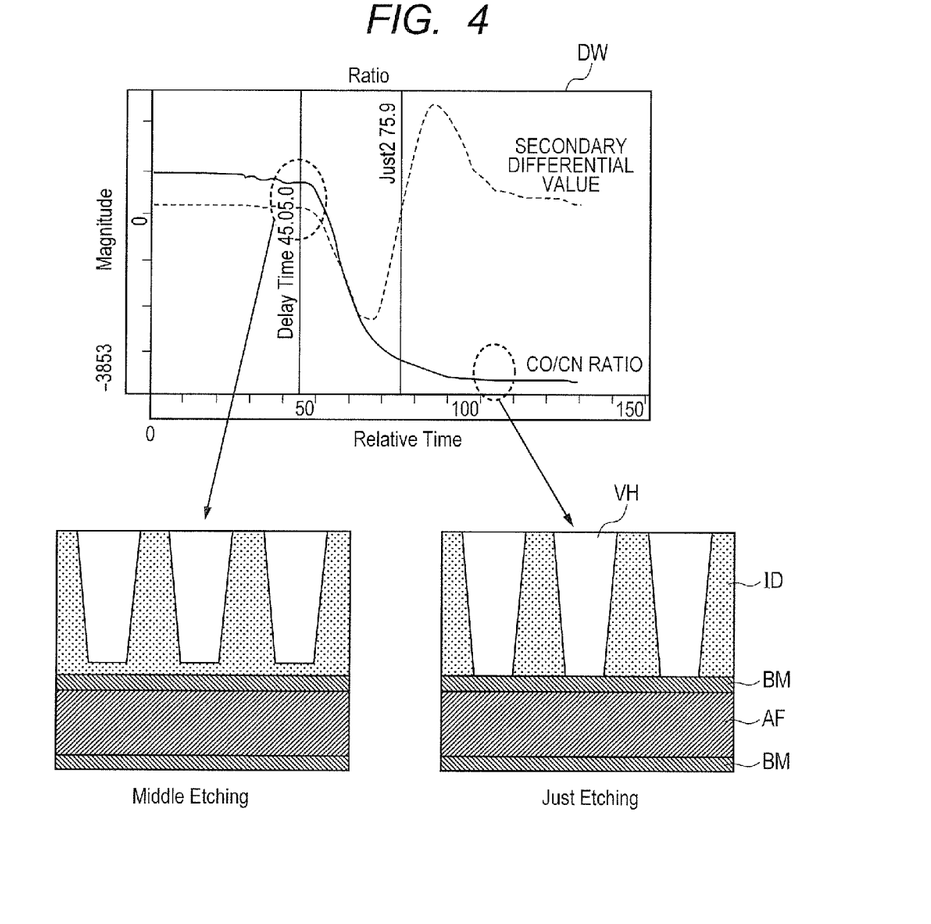
FIG. 4 is a view conceptually illustrating etching end point detection waveforms and the machining states of via holes.
Figure 5:
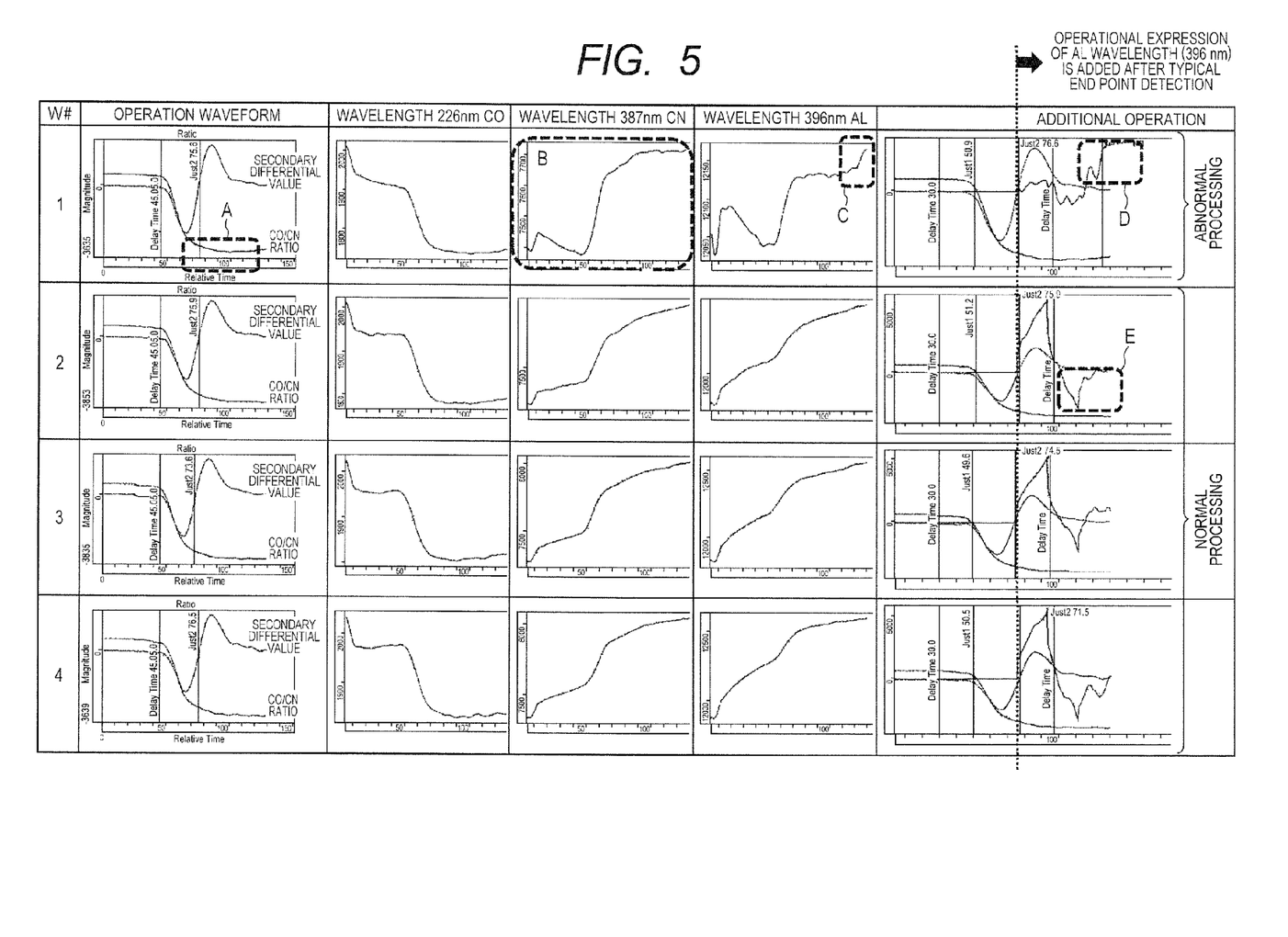
FIG. 5 is graphs each illustrating time series transition of results of an operation for detecting the end point of etching for each detected wavelength.
Figure 8:
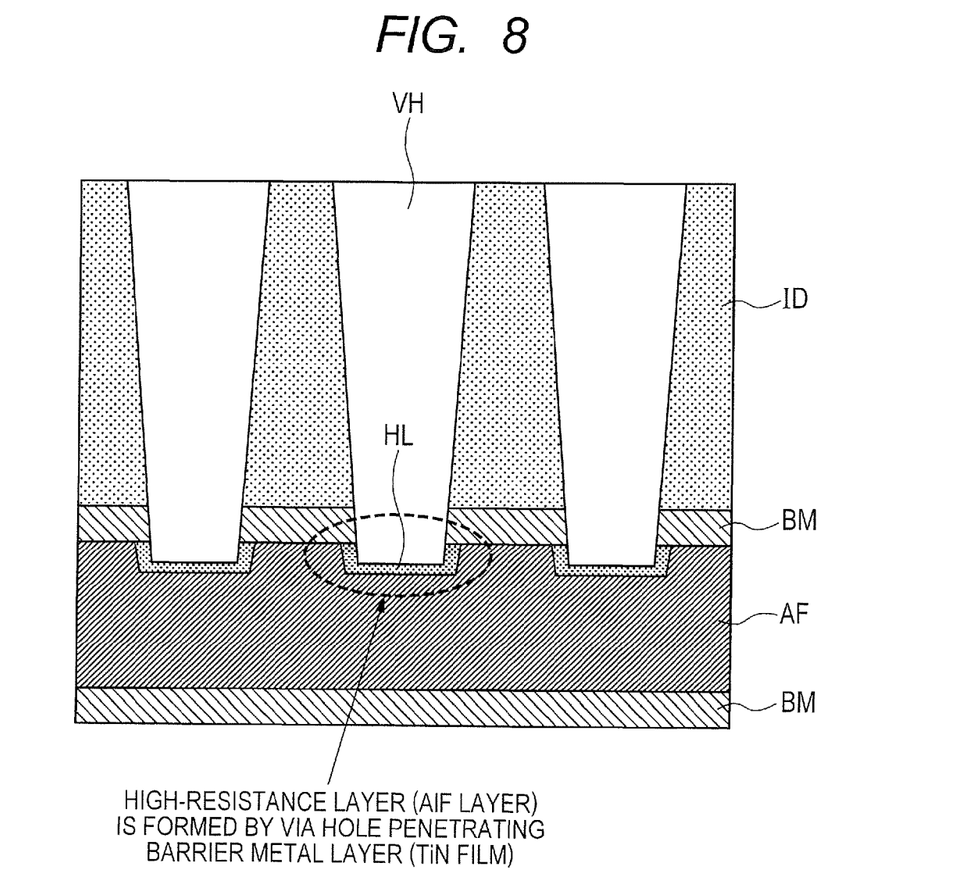
FIG. 8 is a view illustrating a problem caused during via hole etching.

Subsequently, end point detection in via hole etching, when a via hole (contact hole) is formed in an interlayer insulating film, such as a silicon oxide film, will be described with reference to FIGS. 4, 5, and 8. FIG. 4 conceptually illustrates end point detection waveforms and the machining states of via holes. FIG. 5 is graphs each illustrating time series transition of results of an operation for detecting the end point of etching for each detected wavelength. FIG. 8 is a view conceptually illustrating a problem caused during via hole etching.

A problem caused during the related art via hole etching will be first described with reference to FIG. 8. FIG. 8 illustrates a state after a via hole is formed, by dry etching, in an interlayer insulating film ID over metal wiring including three layers of a lower barrier metal BM, an aluminum (AL) film AF, and an upper barrier metal BM. Because the upper barrier metal BM functions as an etching stopper film at via hole etching, it is essentially desirable to end via hole etching when the bottom of a via hole VH reaches the surface of the upper barrier metal BM, or when the etching is performed to the middle of the upper barrier metal BM. However, the etching may be performed to the aluminum (AL) film AF by penetrating the upper barrier metal BM, as illustrated in FIG. 8.

This is caused because the opening area of a via hole is reduced with the miniaturization of a semiconductor product, whereby it becomes difficult to accurately detect an end point by a related art end point detection method. Also, there is the tendency that the diameters of wafers are being increased, and hence an error in etching uniformity, i.e., in an etching rate (etching speed) in the plane of a wafer is likely to become large, whereby in a region where an etching rate is high, the bottom of a via hole may reach the upper barrier metal BM ahead of other regions, and hence even the aluminum (AL) film AF may be etched with the upper barrier metal BM being penetrated with the progress of etching.

If the whole upper barrier metal BM is etched as illustrated in FIG. 8, a fluorine (F) component in etching gas reacts with the aluminum (AL) film, whereby a high-resistance layer (AlF layer) HL is formed in the bottom of the via hole VH, which leads to a conduction defect in a via.

FIG. 4 illustrates end point detection waveforms and machining states of via holes. The horizontal axis of end point detection waveforms DW indicates a relative value (Relative-Time) of etching time, and the vertical axis indicates the magnitude of an operation value in an end point detector. The solid line of the end point detection waveforms DW indicates time series transition of a CO/CN ratio, and the dashed line indicates time series transition of a secondary differential value.

Herein, CO is a reaction product of "C", which is a component in etching gas or in photoresist, and "O", which is a component in a silicon oxide film ($SiO_2$) to be etched; and CN is a reaction product of "C", which is a component in etching gas or in photoresist, and "N", which is a component in a titanium nitride (TiN) film that is the upper barrier metal BM. Accordingly, the etching state of the silicon oxide film (SiO$_2$) can be detected by monitoring the emission intensity of CO ($\lambda$=226 nm). Further, the etching state of the barrier metal BM (TiN film) can be detected by monitoring the emission intensity of CN ($\lambda$=387 nm).

The CO/CN ratio is relatively large at Relative Time of approximately 45, as illustrated in FIG. 4, whereby it is known that the etching of the silicon oxide film (SiO$_2$) is in progress (Middle Etching State in FIG. 4). On the other hand, with the progress of etching, the value of the CO/CN ratio is reduced and a change also becomes small at and after Related Time of approximately 75 to 76, whereby it is known that the etching of the silicon oxide film (SiO$_2$) is being completed. A secondary differential value becomes maximum (inflection point) at Relative Time of approximately 80 to 90, and after this, the CO/CN ratio hardly changes and makes a transition at almost the same level (Just Etching State in FIG. 4). If the dry etching is continued in this state, there is the high risk that the upper barrier metal BM may be penetrated, as illustrated in FIG. 8.

In FIG. 5, a wafer in which the barrier metal BM is penetrated (abnormally processed wafer) and wafers in which the barrier metal BM is not penetrated (normally processed wafers) are compared with each other. The abnormally processed wafer is indicated by the wafer No.1, and the normally processed wafers are indicated by the wafer Nos. 2 to 4.

When the waveforms of CO ($\lambda$=226 nm) in the respective wafers are compared, there is almost no difference between the normally processed wafers and the abnormally processed wafer. With respect to the waveforms of CN ($\lambda$=387 nm), there is a difference between the abnormally processed wafer (B Portion in FIG. 5) and those of the normally processed wafers, but the difference is hardly seen in the related art operation waveforms (a CO/CN ratio and a secondary differential value), whereby it is known that abnormality cannot be detected.

In via hole etching, an end point is typically detected by performing operational processing in combination with a plurality of spectra, such as CO/CN, etc., generated when a silicon oxide film is etched, but in these waveforms, a waveform variation is very small, and hence abnormality cannot be detected.

On the other hand, with respect to the waveforms of AlF ($\lambda$=396 nm), the difference between the abnormally processed wafer and those of the normally processed wafers is large, and particularly in the etching final stage, it is known that the value is greatly increased in the abnormally processed wafer, as illustrated in C Portion in FIG. 5. However, it is very difficult to determine normality or abnormality based only on the difference.

So, when a secondary differential operation of AlF ($\lambda$=396 nm) is added after the end point detection by the related art CO/CN ratio, it is known that the difference between the normally processed wafer and the abnormally processed wafer becomes clearer, as illustrated in D Portion and E Portion in FIG. 5.

In the present embodiment, parallel operational processing is performed at least in an over-etching step by monitoring the waveform of AlF ($\lambda$=396 nm) simultaneously with the waveforms of CO ($\lambda$=226 nm) and CN ($\lambda$=387 nm), in addition to the end point detection by the related art CO/CN ratio (A Portion in FIG. 5). Further, an inflection point is controlled by performing secondary differential processing on AlF ($\lambda$=396 nm). These algorithms are installed in the end point detection controller DS (D Portion and E Portion in FIG. 5). Herein, abnormal processing, i.e., the penetration of a barrier metal can be more accurately detected by performing operational processing on an AL/CN ratio in addition to the operational processing on the related art CO/CN ratio, based on each waveform of monitored CO ($\lambda$=226 nm), CN ($\lambda$=387 nm), and AlF ($\lambda$=396 nm). If the bottom of a via penetrates the barrier metal, the component 'N' in the titanium nitride (TiN) film that is the barrier metal BM is decreased, while the component 'AL' in the metal wiring main body (aluminum film) is increased, and hence the AL/CN ratio exhibits a larger change such that an etching state can be monitored more accurately.

According to the present embodiment, the penetration of a barrier metal, which may be caused during via hole etching, can be detected stably and with high sensitivity, as described above, whereby it becomes possible to prevent manufacture of defective products due to a high-resistance via at an early stage. Further, the reliability of a semiconductor device is also improved by suppressing the formation of a high-resistance via.

Second Embodiment

Figure 6A:
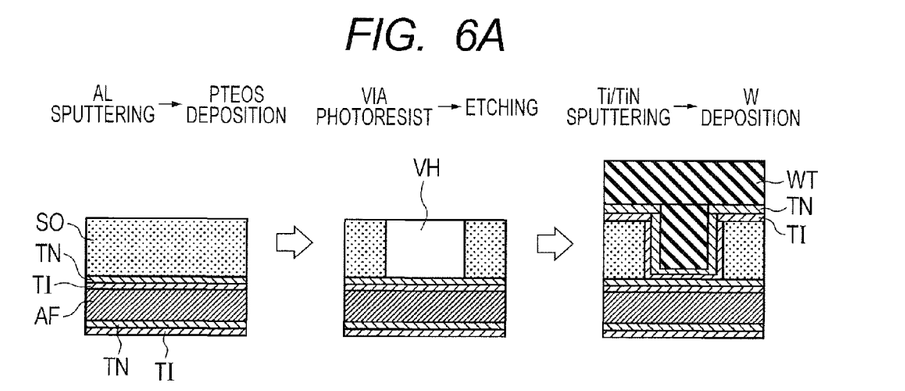
FIG. 6A is views each illustrating part of a manufacturing step of a semiconductor device according to one embodiment of the invention.
Figure 6B:
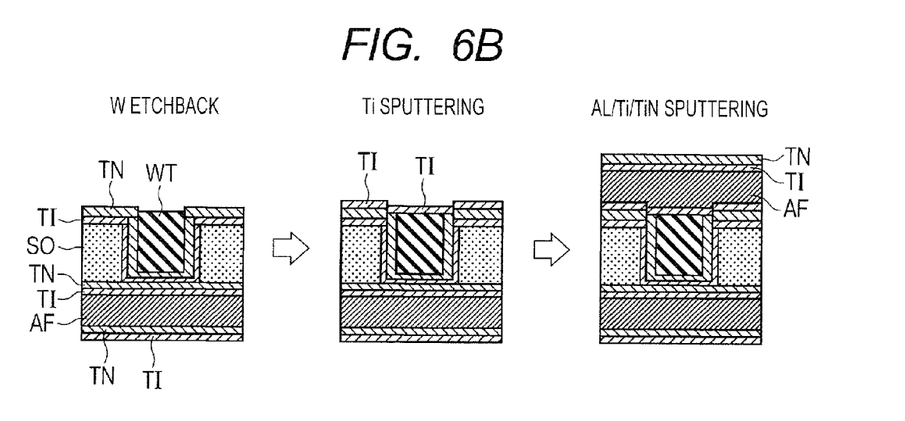
Figure 7A:
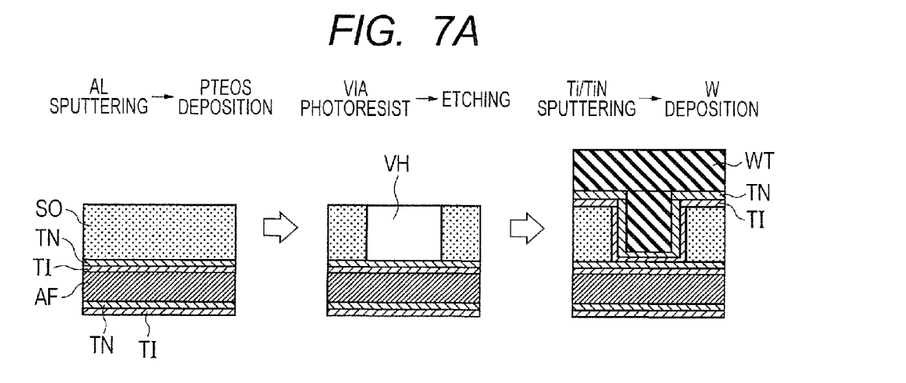
FIG. 7A is views each illustrating part of a manufacturing step of a semiconductor device according to one embodiment of the invention.
Figure 7B:
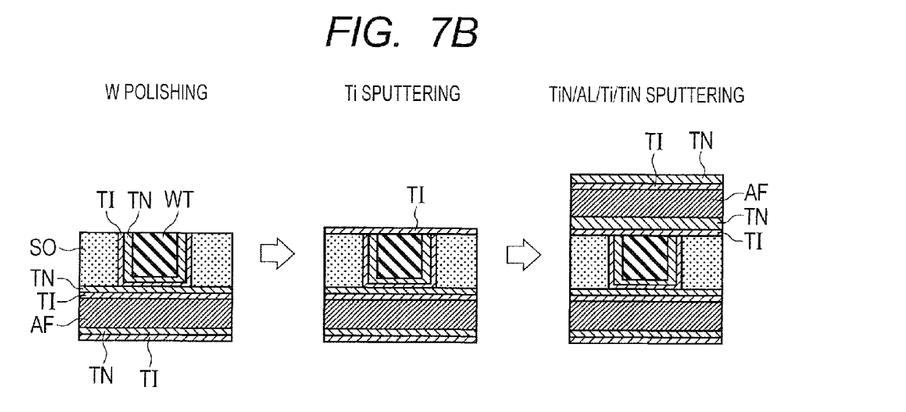
FIG. 7B is views each illustrating part of a manufacturing step of a semiconductor device according to one embodiment of the invention.

A method of manufacturing a semiconductor device by the endpoint detection described in First Embodiment will be described with reference to FIGS. 6A to 7B. Each of FIGS. 6A and 6B illustrates a process flow in which a tungsten (W) via is formed by an etchback process using dry etching. Each of FIGS. 7A and 7B illustrates a process flow in which a tungsten (W) via is formed by CMP polishing (Chemical-Mechanical-Polishing).

The steps of from an AL sputtering step to a PTEOS deposition step will be first described with reference to FIG. 6A. A laminated film is formed over a main surface of a semiconductor substrate (not illustrated) by using a sputtering apparatus, the laminated film including, sequentially from below, a lower titanium (Ti) film TI, a lower titanium nitride (TiN) film TN, the aluminum (AL) film AF, an upper titanium (Ti) film TI, and an upper titanium nitride (TiN) film TN. The thickness of each of the formed films is as follows: the thickness of the lower titanium (Ti) film TI is approximately 8 nm to 12 nm; that of the lower titanium nitride (TiN) film TN is approximately 70 nm to 80 nm; that of the aluminum (AL) film is approximately 350 nm to 450 nm; that of the upper titanium (Ti) film TI is approximately 8 nm to 12 nm; and that of the upper titanium nitride (TiN) film TN is approximately 70 nm to 80 nm. These thicknesses are only illustrative, and are not limited thereto.

Subsequently, a silicon oxide film (SiO$_2$ film) SO including, for example, a PTEOS (Plasma-Tetra-Etyle-Ortho-Silicate) film is formed over the upper titanium nitride (TiN) film TN by using a CVD (Chemical-Vapor-Deposition) apparatus. The thickness of the PTEOS film is approximately 800 nm to 1000 nm.

Subsequently, the steps of from a via photoresist step to an etching step will be described. A photoresist film (not illustrated) is coated over the silicon oxide film SO by a coating apparatus such that a via hole pattern is formed in the photoresist film by lithography. Dry etching processing is performed on the silicon oxide film SO by using the via hole pattern as a mask such that the via hole VH is formed in the silicon oxide film SO.

In the dry etching, the processing conditions (process recipes) as shown in Table 1 are used. In the dry etching conditions in Table 1, a flow rate of etching gas to be introduced into the processing chamber EC and stabilizing time for stabilizing the pressure in the processing chamber EC are set (Step 1). An etching step includes a main etching step (Step 2) and an over-etching step (Step 3). In main etching, etching time is set in accordance with the thickness of the silicon oxide film SO to be etched. In the over-etching step, etching is performed by using end point detection.

For the etching of the silicon oxide film SO, fluorocarbon gas ($C_xF_y$) containing a fluorine (F) component is used as main etching gas. In the dry etching conditions in Table 1, $C_5F_8$ is shown as an example. $CF_4$, $C_3F_8$, $C_4F_8$, or the like, can also be used other than $C_5F_8$.

TABLE 1

| | | Step | | | |
|---|---|---|---|---|---|
| Parameter | | 1 Stabilizing time | 2 Main Etching | 3 Over-etching (End Point Detection Etching) | 4 End | Remarks |
| Upper RF Power (W) | | 0 | 1500~2500 | 1500~2500 | 0 | 60 MHz |
| Lower RF Power (W) | | 0 | 1100~2400 | 1100~2400 | 0 | 2 MHz |
| Process Pressure | (Pa) | 1.33~3.99 | 1.33~3.99 | 1.33~3.99 | 0 | |
|  | (mTorr) | 10~30 | 10~30 | 10~30 | 0 | |
| Etching Gas (sccm) | $C_5F_8$ | 11~17 | 11~17 | 11~17 | 0 | |
| | $O_2$ | 18~26 | 18~26 | 18~26 | 0 | |
| | Ar | 650~750 | 650~750 | 650~750 | 0 | |

Herein, the end point detection method described in First Embodiment is used for the end point detection to be used when the over-etching step (Step 3) in Table 1 is performed. That is, an etching state is monitored by continuously monitoring three wavelengths of at least CO ($\lambda$=226 nm), CN ($\lambda$=387 nm), and AlF ($\lambda$=396 nm) and further by performing secondary differential operational processing on at least AlF ($\lambda$=396 nm) of the above three. Thereby, the via hole VH can be prevented, at over-etching, from being formed to penetrate the titanium nitride (TiN) film TN and the titanium (Ti) film TI that are base films of the silicon oxide film SO.

Further, even if the via hole VH penetrates the titanium nitride (TiN) film TN and the titanium (Ti) film TI, abnormal processing can be determined from a secondary differential value of AlF ($\lambda$=396 nm), whereby manufacture of defective products, occurring due to a high-resistance via, can be prevented.

Subsequently, the steps of from a Ti/TiN sputtering step to a W deposition step will be described. A titanium (Ti) film TI and a titanium nitride (TiN) film TN are formed by a sputtering apparatus so as to cover the surfaces of both the inside of the via hole VH and the silicon oxide film SO. The thicknesses of the formed films are as follows: the thickness of the titanium (Ti) film TI is approximately 8 nm to 12 nm; and that of the titanium nitride (TiN) film TN is approximately 70 nm to 80 nm. Subsequently, a tungsten (W) film WT is formed over the titanium nitride (TiN) film TN by using a CVD apparatus so as to fill up the via hole VH. The thickness of the tungsten (W) film WT is approximately 450 nm to 550 nm.

A W etchback step will be described with reference to FIG. 6B.

The unnecessary tungsten (W) film WT over the titanium nitride (TiN) film TN is etched back by using a dry etching apparatus, so that the tungsten (W) film WT, other than that in the via hole VH, is removed. At this time, a hollow, which is referred to as a recess, is formed in the surface of the tungsten (W) film WT in the via hole VH.

Subsequently, a Ti sputtering step will be described. A titanium (Ti) film TI is formed over both the surface of the titanium nitride (TiN) film TN and the tungsten (W) film WT in the via hole VH by using a sputtering apparatus. The thickness of the titanium (Ti) film TI is approximately 8 nm to 12 nm.

Subsequently, an AL/Ti/TiN sputtering step will be described. An aluminum (AL) film AF is formed by using a CVD apparatus. The thickness of the aluminum (AL) film AF is approximately 350 nm to 450 nm. Subsequently, a titanium (Ti) film TI and a titanium nitride (TiN) film TN are formed, sequentially from below, over the aluminum (AL) film AF by using a sputtering apparatus. The thicknesses of these films are as follows: the thickness of the titanium (Ti) film TI is approximately 8 nm to 12 nm; and that of the titanium nitride (TiN) film TN is approximately 80 nm to 120 nm.

The via structure illustrated on the right side of FIG. 6B is formed through the steps described above. According to the manufacturing method of a semiconductor device illustrated in FIGS. 6A and 6B, the end point detection method described in First Embodiment is used for via hole etching, and hence: the penetration of the titanium nitride (TiN) film TN and the titanium (Ti) film TI, which form a barrier metal for the lower wiring, can be prevented; formation of a high-resistance via can be suppressed; and a semiconductor device with high reliability can be manufactured.

A manufacturing method using a W-CMP apparatus will be described with reference to FIGS. 7A and 7B. A main difference between the manufacturing method illustrated in FIGS. 6A and 6B and that illustrated in FIGS. 7A and 7B is that the unnecessary tungsten (W) film WT, other than that in the via hole VH, is removed by an etchback process or by W polishing, and hence description will be made by omitting common parts. Although the thicknesses of various films to be formed are different according to each process generation of products in which each manufacturing method is adopted, it is not directly related to the gist of the present application, and hence detailed description will be omitted in FIGS. 7A and 7B.

FIG. 7A illustrates the steps of from an AL sputtering step to a W deposition step, similarly to FIG. 6A. The steps are basically the same as those of FIG. 6A, other than the differences between the thicknesses of various films. Accordingly, the processing conditions (process recipes) in Table 1 are used for the via hole etching performed between a via photoresist step and an etching step in FIG. 7A, and the end point detection method described in First Embodiment is used for the end point detection performed when an over-etching step (Step 3) is performed.

That is, an etching state is monitored by continuously monitoring three wavelengths of at least CO ($\lambda$=226 nm), CN ($\lambda$=387 nm), and AlF ($\lambda$=396 nm) and further by performing secondary differential operational processing on at least AlF (λ=396 nm) of the above three. Thereby, the via hole VH can be prevented from being formed to penetrate the titanium nitride (TiN) film TN and the titanium (Ti) film TI that are base films of the silicon oxide film SO, which may be caused during over-etching, similarly to the manufacturing method illustrated in FIGS. 6A and 6B.

The unnecessary tungsten (W) film WT, other than that in the via hole VH, is removed by CMP polishing with the use of a W-CMP apparatus, as illustrated in FIG. 7B. Although the titanium nitride (TiN) film TN over the silicon oxide film SO functions as a stopper film when the CMP polishing is being performed, a damage is caused by the CMP polishing, and hence it is removed by wet etching, or the like, after the CMP polishing.

Subsequently, a titanium (Ti) film TI is formed over the silicon oxide film SO, the titanium (Ti) film TI, and the titanium nitride (TiN) film TN by using a sputtering apparatus.

Subsequently, a titanium nitride (TiN) film is formed over the titanium (Ti) film TI by similarly using a sputtering apparatus, and then an aluminum (AL) film AF is formed by using a CVD apparatus, and finally a titanium (Ti) film TI and a titanium nitride (TiN) film TN are formed over the aluminum (AL) film AF by using a sputtering apparatus, whereby the via illustrated on the right side of FIG. 7B is formed. According to the manufacturing method of a semiconductor device illustrated in FIGS. 7A and 7B, the end point detection method described in First Embodiment is used for via hole etching, and hence: the penetration of the titanium nitride (TiN) film TN and the titanium (Ti) film TI, which form a barrier metal for the lower wiring, can be prevented; formation of a high-resistance via can be suppressed; and a semiconductor device with high reliability can be manufactured.

The metal wiring having a laminated structure, which has been described in First and Second Embodiments, has, as an example, a 5-layer structure in which a titanium (Ti) film, a titanium nitride (TiN) film, an aluminum (AL) film, a titanium (Ti) film, and a titanium nitride (TiN) film are formed sequentially from below; however, the metal wiring should not be limited thereto, and for example, the upper and lower titanium (Ti) films may be omitted. The metal wiring may have, for example, a 3-layer structure including a titanium nitride (TiN) film, an aluminum (AL) film, and a titanium nitride (TiN) film.

Although each Embodiment has been described by using an example in which via hole etching is used when a via hole (contact hole) is formed in an interlayer insulating films, such as a silicon oxide film, each Embodiment is also effective when a gate electrode is formed, for example, by etching a polysilicon (Poly-Si) film over a gate oxide film.

When the polysilicon (Poly-Si) film is etched, the light emission of a product, which has been produced by a reaction of a component in the polysilicon (Poly-Si) film to be etched with an etching gas component, is monitored. In addition, when over-etching is performed, the light emission of a product, which has been produced by a reaction of a component in a gate oxide film ($SiO_2$ film) that is a base film of a polysilicon (Poly-Si) film with an etching gas component, is monitored and a secondary differential value is monitored, whereby a defect in which the gate oxide film is penetrated can be prevented.

The invention made by the present inventors has been specifically described above based on preferred embodiments, but the invention should not be limited to the preferred embodiments, and it is needless to say that various modifications may be made to the invention within a range not departing from the gist of the invention.

What is claimed is:

1. A manufacturing method of a semiconductor device, comprising the steps of:
   (a) forming, over a main surface of a semiconductor substrate, laminated wiring including, sequentially from below, three layers of a titanium nitride film, an aluminum film, and a titanium nitride film;
   (b) forming an insulating film over the laminated wiring so as to cover the laminated wiring;
   (c) coating a photoresist film over the insulating film in order to form a via hole pattern by lithography; and
   (d) forming a via hole in the insulating film by dry etching using the via hole pattern as a mask,
   wherein, when the dry etching of the insulating film is performed, an end point of the dry etching of the insulating film is detected by monitoring emission intensities of at least CO and CN.

2. The manufacturing method of a semiconductor device according to claim 1,
   wherein the insulating film is a silicon oxide film, and the dry etching is performed by using etching gas containing a fluorine component.

3. The manufacturing method of a semiconductor device according to claim 1,
   wherein operational processing is performed using the monitored emission intensities of CO and CN, and the end point of the dry etching of the insulating film is detected based on a result of the operational processing.

4. The manufacturing method of a semiconductor device according to claim 3,
   wherein the end point of the dry etching of the insulating film is detected based on a CO/CN ratio and an Al/CN ratio.

5. The manufacturing method of a semiconductor device according to claim 1,
   wherein the dry etching of the insulating film includes a main etching step and an over-etching step, and emission intensity of AlF is monitored at least in the over-etching step.

6. The manufacturing method of a semiconductor device according to claim 5,
   wherein a state of the dry etching is monitored by performing secondary differential processing using the monitored emission intensity of AlF and by controlling an inflection point of a calculated secondary differential value.

7. The manufacturing method of a semiconductor device according to claim 6,
   wherein, when a secondary differential value calculated from the emission intensity of AlF becomes more than a preset value, it is determined that abnormality has been caused in the dry etching, and an alarm is issued.

8. A method of detecting an end point of dry etching comprising:
   monitoring emission intensities of at least CO and CN of emission spectra of plasma to be used for dry etching; and
   detecting an end point of the dry etching based on the monitored emission intensities of CO and CN.

9. The method of detecting an end point of dry etching according to claim 8,
   wherein the dry etching is used for forming a via hole in a silicon oxide film formed over aluminum wiring, and is performed by using etching gas containing a fluorine component.

10. The method of detecting an end point of dry etching according to claim 8,
wherein operational processing is performed using the monitored emission intensities of CO and CN, and an end point of dry etching is detected based on a result of the operational processing.

11. The method of detecting an end point of dry etching according to claim 10,
wherein an end point of dry etching is detected based on a CO/CN ratio and an Al/CN ratio.

12. The method of detecting an end point of dry etching according to claim 8,
wherein the dry etching includes a main etching step and an over-etching step, and emission intensity of AlF is monitored at least in the over-etching step.

13. The method of detecting an end point of dry etching according to claim 12,
wherein a state of the dry etching is monitored by performing secondary differential processing using the monitored emission intensity of AlF and by controlling an inflection point of a secondary differential value from the secondary differential processing.

14. The method of detecting an end point of dry etching according to claim 13,
wherein, when a secondary differential value calculated from the emission intensity of AlF becomes more than a preset value, it is determined that abnormality has been caused in the dry etching, and an alarm is issued.

15. A manufacturing method of a semiconductor device, comprising the steps of:
(a) forming, over a main surface of a semiconductor substrate, laminated wiring including, sequentially from below, three layers of a titanium nitride film, an aluminum film, and a titanium nitride film;
(b) forming an insulating film over the laminated wiring so as to cover the laminated wiring;
(c) coating a photoresist film over the insulating film in order to form a via hole pattern by lithography; and
(d) forming a via hole in the insulating film by dry etching using the via hole pattern as a mask,
wherein, when the dry etching of the insulating film is performed, an end point of the dry etching of the insulating film is detected by monitoring emission intensities of at least two of CO, CN and AlF.

* * * * *